US011083606B2

(12) United States Patent
Collins et al.

(10) Patent No.: US 11,083,606 B2
(45) Date of Patent: Aug. 10, 2021

(54) ENDOGRAFT DELIVERY DEVICE ASSEMBLY

(71) Applicant: Cook Medical Technologies LLC, Bloomington, IN (US)

(72) Inventors: James Collins, Paddington (AU); Logan Smith, Mount Gravatt (AU)

(73) Assignee: Cook Medical Technologies LLC, Bloomington, IN (US)

( * ) Notice: Subject to any disclaimer, the term of this patent is extended or adjusted under 35 U.S.C. 154(b) by 402 days.

(21) Appl. No.: 16/186,174

(22) Filed: Nov. 9, 2018

(65) Prior Publication Data
US 2019/0167456 A1 Jun. 6, 2019

Related U.S. Application Data

(60) Provisional application No. 62/594,911, filed on Dec. 5, 2017.

(30) Foreign Application Priority Data

Dec. 5, 2017 (AU) .................................. 2017904881

(51) Int. Cl.
*A61F 2/966* (2013.01)
*A61F 2/95* (2013.01)
(Continued)

(52) U.S. Cl.
CPC .................. *A61F 2/95* (2013.01); *A61F 2/07* (2013.01); *A61F 2/848* (2013.01); *A61F 2/966* (2013.01);
(Continued)

(58) Field of Classification Search
CPC .... A61F 2/07; A61F 2/95; A61F 2/954; A61F 2/9517; A61F 2/962; A61F 2/966;
(Continued)

(56) References Cited

U.S. PATENT DOCUMENTS 6,471,722 B1 10/2002 Inoue
6,878,161 B2 4/2005 Lenker
(Continued)

FOREIGN PATENT DOCUMENTS

AU 2012258395 B1 7/2013
CN 105943212 A 9/2016
(Continued)

*Primary Examiner* — Diane D Yabut
*Assistant Examiner* — Christian D Knauss
(74) *Attorney, Agent, or Firm* — Brinks Gilson & Lione

(57) ABSTRACT

An endovascular delivery device comprises an outer handle with a track; an inner handle moveable relative to the outer handle; a tip assembly slider mounted on the track; the tip assembly having a top cap and a retriever, the top cap comprising a mouth receiving a proximal portion of the endograft and closable by the retriever; a connector extending from the tip to the inner handle and including a distal portion slidably engaging the inner handle; a pusher catheter extending from the outer handle assembly; a guidewire catheter; a distal trigger wire operable to release the distal end of the endograft; a proximal trigger wire release slider mounted on the track and movable from an initial to a triggered position, wherein the tip assembly slider engages the trigger wire release slider to prevent distal movement until the trigger wire release slider is moved distally.

14 Claims, 18 Drawing Sheets

(51) Int. Cl.
*A61F 2/07* (2013.01)
*A61F 2/848* (2013.01)
*A61F 2/06* (2013.01)

(52) U.S. Cl.
CPC ....... *A61F 2/9517* (2020.05); *A61F 2002/061* (2013.01); *A61F 2002/9528* (2013.01); *A61F 2002/9534* (2013.01); *A61F 2002/9665* (2013.01)

(58) Field of Classification Search
CPC ...... A61F 2002/9505; A61F 2002/9511; A61F 2002/9665
See application file for complete search history.

(56) References Cited

U.S. PATENT DOCUMENTS

| | | | |
|---|---|---|---|
| 7,435,253 | B1 | 10/2008 | Hartley et al. |
| 8,852,266 | B2 | 10/2014 | Brooks et al. |
| 9,095,683 | B2 | 8/2015 | Hall et al. |
| 9,220,619 | B2 | 12/2015 | Ramos et al. |
| 9,370,421 | B2 | 6/2016 | Crisostomo et al. |
| 9,486,350 | B2 | 11/2016 | Argentine |
| 9,504,555 | B2 | 11/2016 | Hartley et al. |
| 9,849,016 | B2 | 12/2017 | Beard et al. |
| 2003/0187469 | A1 | 10/2003 | Olson |
| 2006/0129181 | A1 | 6/2006 | Callol et al. |
| 2007/0299499 | A1* | 12/2007 | Hartley .................. A61F 2/962 623/1.11 |
| 2009/0099650 | A1* | 4/2009 | Bolduc .................... A61F 2/07 623/1.36 |
| 2011/0077731 | A1 | 3/2011 | Lee et al. |
| 2011/0307048 | A1* | 12/2011 | Ivancev .................. A61F 2/95 623/1.11 |
| 2014/0052232 | A1 | 2/2014 | Cragg et al. |
| 2014/0121750 | A1 | 5/2014 | Hadley et al. |
| 2015/0230955 | A1 | 8/2015 | Farag Eells |
| 2015/0335452 | A1 | 11/2015 | Rao |
| 2016/0338864 | A1 | 11/2016 | Vad |
| 2018/0178007 | A1 | 6/2018 | Shuros |
| 2020/0345524 | A1 | 11/2020 | Collins et al. |

FOREIGN PATENT DOCUMENTS

| | | |
|---|---|---|
| EP | 18275158.6 | 5/2019 |
| WO | 2008042270 A1 | 4/2008 |
| WO | 2011159504 A1 | 12/2011 |

* cited by examiner

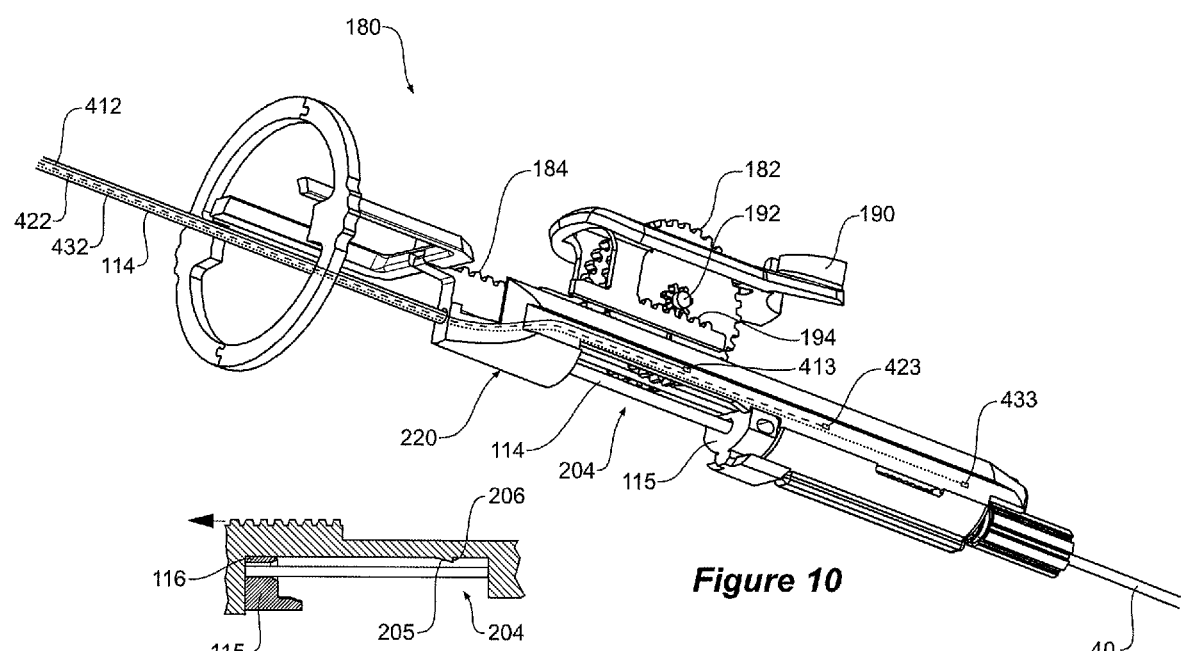
*Figure 10*
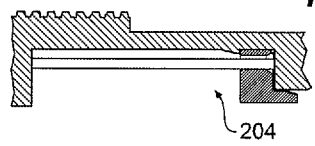
*Figure 11A*
*Figure 11B*

ENDOGRAFT DELIVERY DEVICE ASSEMBLY

CROSS REFERENCE TO RELATED APPLICATIONS

The present application claims priority from U.S. provisional application 62/594,911 and Australian patent application 2017904881, the disclosures of both of which are incorporated herein by reference.

FIELD OF THE INVENTION

The present invention relates to endografts and their delivery systems. In particular, the present invention relates to delivery device assemblies capable of delivering stent grafts into the vascular system.

BACKGROUND OF THE INVENTION

Stent graft and delivery devices are used in aortic intervention. They are used by vascular surgeons to treat aneurysms and to repair regions of the aorta, including the aortic arch, the thoracic aorta, the abdominal aorta and the aortic bifurcation.

Delivery devices allow deployment of intraluminal prostheses or endografts into the lumen of a patient from a remote location.

Numerous devises and procedures have been developed that involve the percutaneous insertion of prostheses into a body lumen, such as a blood vessel or duct of a patient's body. Such prostheses may be introduced into the lumen by a variety of known techniques. For example, a wire guide may be introduced into a blood vessel using the Seldinger technique. This technique involves creating a surgical opening in the vessel with a needle and inserting a wire guide into the vessel through a bore of the needle. The needle can be withdrawn, leaving the wire guide in place. A delivery device is then inserted over the wire guide and into the vessel. The delivery device may be used in conventional fashion to insert into the blood vessel a variety of prostheses, such as stents, stent grafts, catheters, cardiac leads, balloons, and the like.

For example, the delivery device may be used to deliver and deploy an expandable prosthesis, such as a stent graft, to an aneurysmal blood vessel site. A stent graft is usually formed from a tubular body of a biocompatible graft material with one or more stents mounted into or onto the tubular body to provide support therefor. The stents may be balloon expandable stents and/or self-expanding stents. The deployment of the prosthesis into the lumen of a patient from a remote location by the use of an introducer delivery and deployment device is described in, for example, U.S. Pat. No. 7,435,253 to Hartley entitled "A Prosthesis and a Method and Means of Deploying a Prosthesis," which is incorporated herein by reference in its entirety Delivery devices are configured to retain a prosthesis in a delivery configuration during delivery to the desired deployment site. The delivery catheter typically includes an inner catheter or cannula spaced from an outer sheath to provide a prosthesis retaining region for receiving or holding the prosthesis. The prosthesis is loaded onto an inner cannula along the prosthesis retaining region, with an outer sheath retaining the prosthesis in the delivery configuration. After the delivery device is delivered to the desired deployment site, the prosthesis may be deployed, for example with retraction of the outer sheath relative to the inner cannula away from the prosthesis to allow for expansion thereof. Accurate placement of an appropriately sized prosthesis generally sufficiently covers the target site for treatment and the ends of the prosthesis are typically engaged with healthy tissue of the body lumen.

Endovascular delivery devices require significant expertise and experience to operate. Correct sequencing of various manual operations performed outside the body (at a distal end of a delivery device) are required for successful and optimum deployment of an endograft. It is desirable to make operation as intuitive and foolproof as possible.

SUMMARY OF THE INVENTION

The present invention seeks to provide an improved endograft and delivery device assembly.

According to an aspect of the invention, an endograft delivery device is provided, the assembly comprising an endovascular delivery device for delivering an endograft, the device having a proximal end and a distal end, the delivery device comprising:

an outer handle portion mounted to the distal end of the delivery device, the outer handle portion having a body portion and a track extending distally from the body portion;

an inner handle portion, the inner handle portion slidably moveable within, and with respect to, the outer handle portion from a distal position to a proximal position;

a tip assembly slider, mounted on the track for sliding movement with respect to the track;

a tip assembly at the proximal end of the delivery device;

a pusher catheter extending proximally from the outer handle portion;

a guide wire catheter extending through the inner handle portion and through the pusher catheter, the guide wire catheter being affixed at a distal end thereof to the inner handle portion and being affixed at a proximal end thereof to the tip assembly; and an endograft receiving portion for receiving the endograft between the tip assembly and the pusher catheter;

wherein the tip assembly slider is operably connected to the inner handle portion such that distal sliding movement of the tip assembly slider slides the tip assembly towards the pusher catheter.

Advantageously, the device comprises a distal trigger wire for releasably retaining a distal end of the endograft, whereby distal movement of the tip assembly slider pulls the distal trigger wire thereby releasing the distal end of the endograft.

Preferably, the device comprises a proximal trigger wire release slider mounted on the track distally of the tip assembly slider, for sliding movement with respect to the track from an initial position to a triggered position; and a proximal trigger wire for releasably retaining a proximal end of the endograft loadable on the endograft receiving portion, whereby distal movement of the proximal trigger wire release slider pulls the proximal trigger wire thereby releasing the proximal end of the endograft.

The tip assembly slider may engage the proximal trigger wire release slider such that it cannot be moved distally until after the proximal trigger wire release slider has been moved distally.

Advantageously, the tip assembly comprises a top cap and a retriever, the tip assembly having an open configuration and a closed configuration.

The top cap preferably comprises a distally facing mouth, whereby in the open configuration, the mouth is open for receiving a proximal portion of the endograft, and in the closed configuration, the mouth is closed by the retriever.

The device may comprise a connector extending from the tip assembly to the inner handle portion, the connector including a distal portion slidably engageable with the inner handle portion.

The device may comprise a tip assembly actuator operably connected to the inner handle portion; and an actuator receiving portion 184 on the inner handle portion, the actuator receiving portion slidably drivable by the tip assembly actuator in a proximal direction.

The actuator receiving portion may comprise a rack.

Preferably, the tip assembly actuator is actuatable to move the inner handle portion proximally with respect to the outer handle portion thereby actuating the tip assembly from the first configuration to the second configuration.

The connector advantageously comprises a tube co-axially mounted over the guide wire catheter, the tube joining the tip retriever to the connector distal end.

BRIEF DESCRIPTION OF DRAWINGS

Embodiments of the present invention are described below, by way of example only, with reference to the accompanying drawings, in which:

FIG. 10 is a detailed isometric view showing the inner handle portion of the device shown in FIGS. 1A to 4A and FIGS. 8A to 8D;

FIGS. 11A and 11B are diagrammatic views showing a portion of the inner handle assembly shown in FIG. 10 together with parts of a tip retriever actuator;

DESCRIPTION OF THE PREFERRED EMBODIMENTS

Figure 1A:
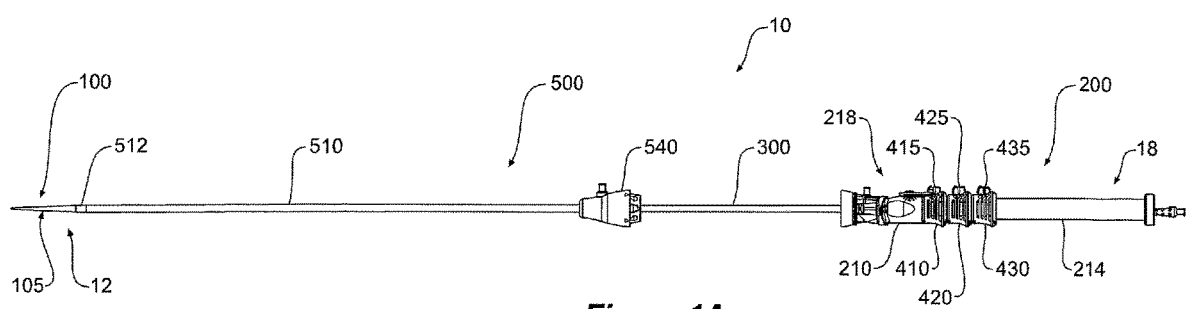
FIG. 1A shows a first embodiment of an endovascular delivery device according to the invention in a side view.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow. Thus, in this description, the term "proximal" refers to the end of the delivery device that carries the endograft and that in use is located within the patient's vasculature at the treatment site. The term "distal" refers to the end of the delivery device that remains outside the patient during the procedure and that is manipulated by the physician.

For the purposes of understanding the principles taught herein, reference will now be made to the embodiments illustrated in the drawings, and specific language will be used to describe them. It is to be understood that the Figures are, in some cases, schematic and do not show the various components in their actual scale. In many instances, the Figures show scaled up components to assist the reader.

Referring now to FIGS. 1A, 1B, 2A, 2B, 3A, 3B, 4A and 4B, there is shown a delivery device 10 for the percutaneous insertion into the artery (or other bodily lumen) of prostheses such as stents, stent grafts, catheters, cardiac leads, balloons, and the like, according to a first embodiment of the invention. It can be seen from FIG. 1B that the delivery device 10 is loaded with an endograft or stent graft 5.

Figure 1B:
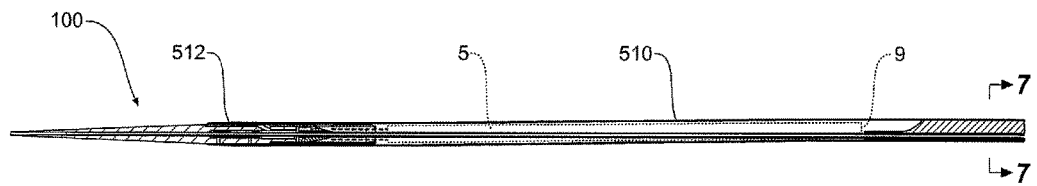
FIG. 1B shows a proximal end of the device of FIG. 1A.

Referring first to FIGS. 1A and 1B, it can be seen that the device has a proximal end 12 and a distal end 18. The delivery device 10 has an outer handle portion 210 located at its distal end 18. The outer handle portion 210 has a body portion 218 and a track 214 extending distally from the body portion 218. The delivery device 10 also has an inner handle portion 220 which is shown in FIGS. 8A, 8B, 8C and FIG. 10. The inner handle portion 220 is slidably moveable within, and with respect to, the outer handle portion 210 from a distal position to a proximal position, as can be seen progressively in FIGS. 8A and 8B.

Figure 12A:
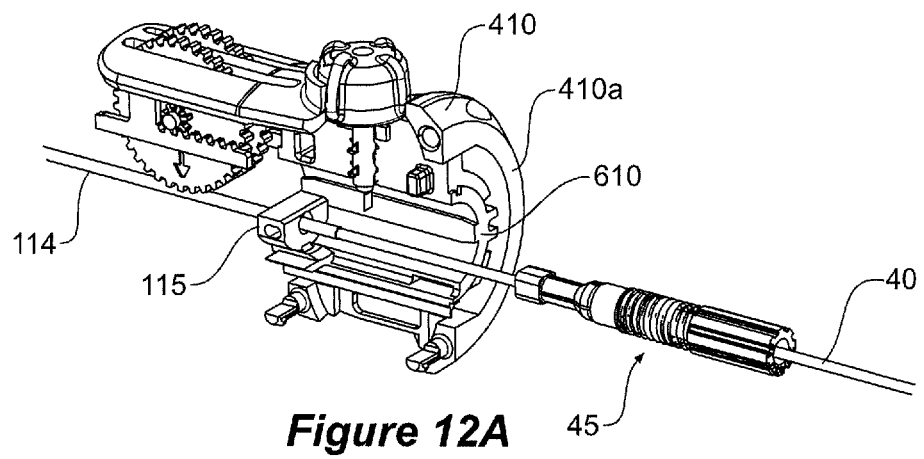
FIG. 12A is a detailed isometric view showing components of the device shown in FIG. 1A, including a tip assembly slider.
Figure 12B:
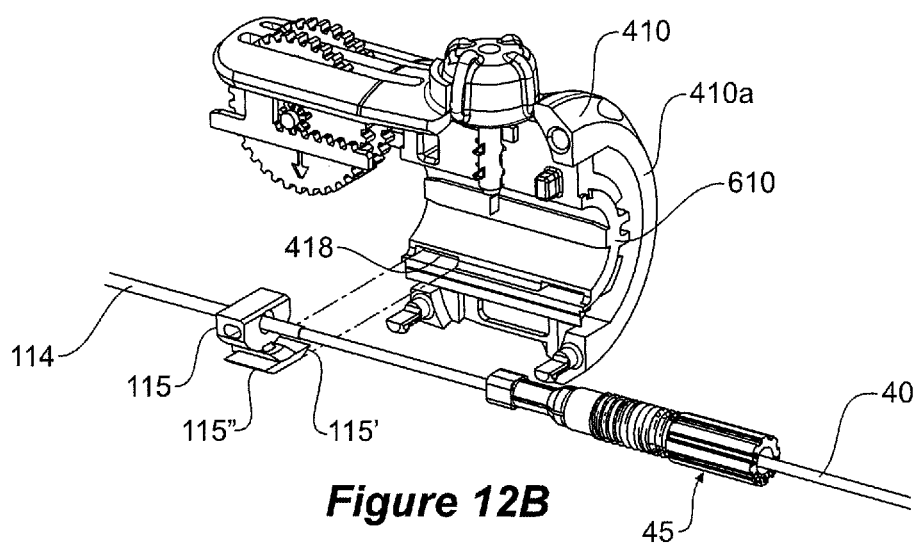
FIG. 12B is a similar view to that of FIG. 12A, showing the components in an exploded view.

A tip assembly slider 410 is mounted on the track 214 for sliding movement with respect to the track 214, as is shown in FIG. 1A and in further detail in FIGS. 12A and 12B. While various constructions may be used, it is convenient to provide a generally part-cylindrical track having a longitudinally extending slot 219 (the same as that shown in FIGS. 15 and 17). The tip assembly slider 410 is mounted on the track 214 and includes an outer arcuate portion 410a and an inner arcuate portion 610, shown most clearly in FIGS. 12A to 12C. The tip assembly slider 410 is finger graspable for sliding movement with respect to the track 214.

Figure 6A:
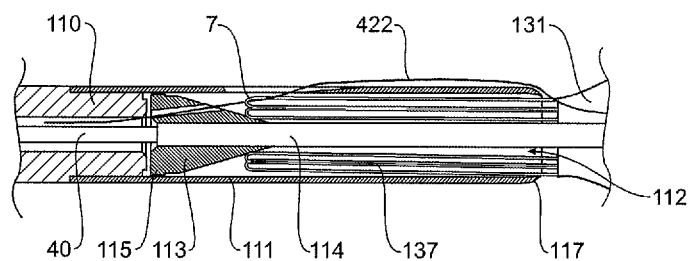
FIG. 6A is an even more detailed view of a proximal end of the device of the first embodiment of the invention showing a tip assembly.
Figure 6B:
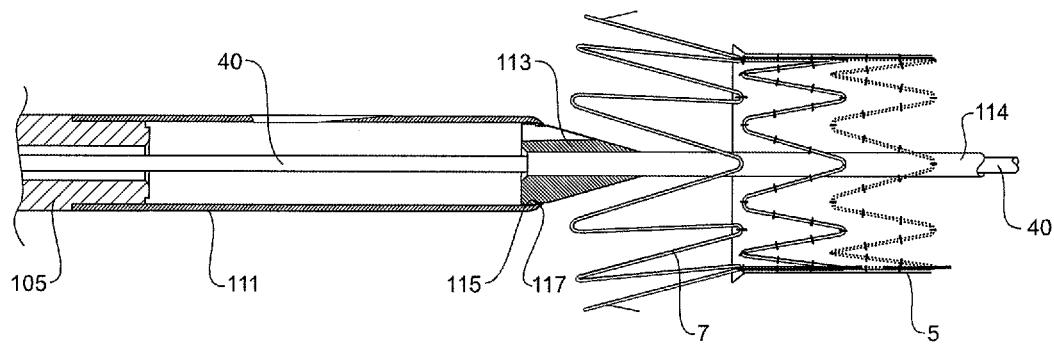
FIG. 6B is similar to that of FIG. 6A but shows the tip assembly in a second position.

A tip assembly 100 is located at the proximal end 12 of the delivery device 10, as is shown in FIGS. 1A and 1B. Further detail is shown in FIGS. 6A and 6B. In particular, it can be seen that an exposed stent 7 at a proximal end of the endograft 5 is captured by a proximal trigger wire 422, as is shown in FIG. 6A.

FIG. 10 shows distal, proximal and reducing trigger wires (412, 422 and 432 respectively) and their terminal ends 413, 423 and 433 respectively.

Figure 8A:
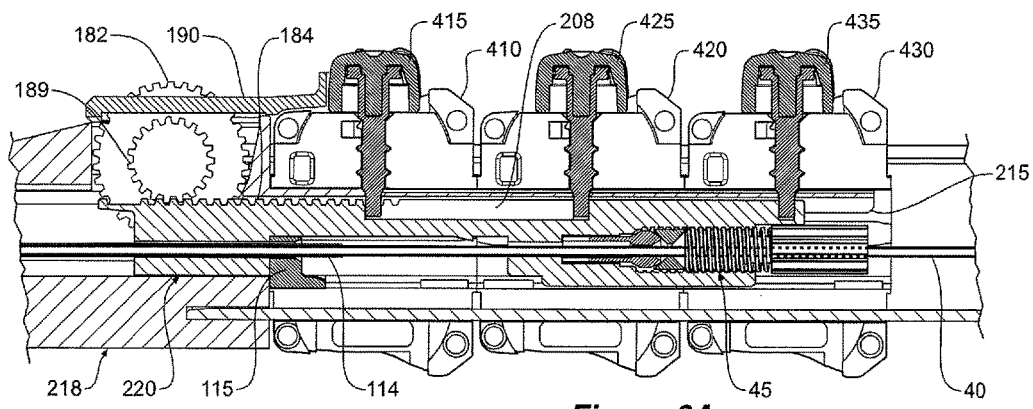
FIGS. 8A to 8D are detailed cross-sectional views of the outer and inner handle portions of the device shown in FIGS. 1A to 4A in progressive positions.

The delivery device 10 also has a pusher catheter 300 extending proximally from the outer handle portion 210 towards the tip assembly 100, as can be seen in FIGS. 1B, 2B, 3B and 4B. A distal end of the pusher catheter is attached to the outer handle portion 210. A guide wire catheter 40 extends through the inner handle portion 220 and through the pusher catheter 300. The guide wire catheter 40 is affixed at a distal end thereof to the inner handle portion 220 and is affixed at a proximal end thereof to the tip assembly 100. A pin vice assembly 45, such as is shown in FIGS. 8A, 12A and 12B can be used. Such a pin vice assembly attaches to the inner handle portion 220, as is shown in FIGS. 8A and 10. Various pin vice constructions may be used, such as is described in U.S. Pat. No. 7,435,253 to Hartley referred to above where the pin vice has a screw cap which, when screwed in, clamps vice jaws against the thin walled metal tube (guide wire catheter).

In other embodiments, not shown, gluing, crimping or other attachment means may be used to secure the guide wire catheter 40 to the inner handle portion 220.

Figure 7:
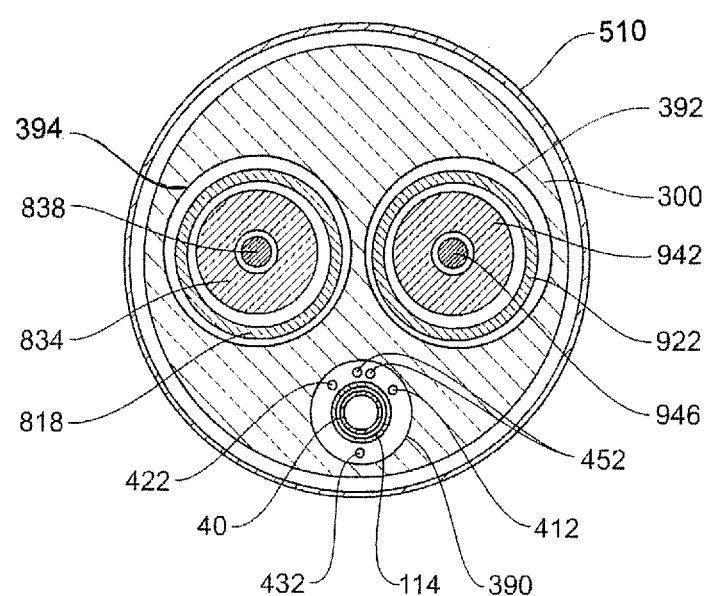
FIG. 7 is a cross-sectional view taken through section lines 7-7 shown in FIG. 1B.

The pusher catheter is also shown in a cross-sectional view in FIG. 7 where it is shown surrounded by a sheath 510. The particular pusher catheter 300 of this embodiment has three longitudinally extending lumens. A first lumen is the guide wire lumen 390 and this lumen is off-set from the centre of the pusher catheter to allow for two auxiliary lumens 392 and 394. The guide wire lumen 390 has passing through it the guide wire catheter 40 and coaxially around that the connector or retrieval catheter 114. Also in the guide wire lumen 390 are trigger wires, including a proximal trigger wire 422, a diameter reducing ties trigger wire 432, and a distal trigger wire 412. Further auxiliary guides 452 are also shown that may be used in some applications.

The auxiliary lumen 394 has an access sheath 818 extending through it and the dilator 834 and guide wire 838 extend through the access sheath 818. Similarly, the auxiliary lumen 392 has an access sheath 922 extending through it and the dilator 942 and guide wire 946 extend through the access sheath 922.

The sheath 510 is part of a sheath assembly 500, as is shown in FIGS. 1A to 4A. These figures also show a valve body 540 at a distal end of the sheath assembly 500. FIG. 4B shows a proximal end 512 of the sheath 510.

Figure 2A:
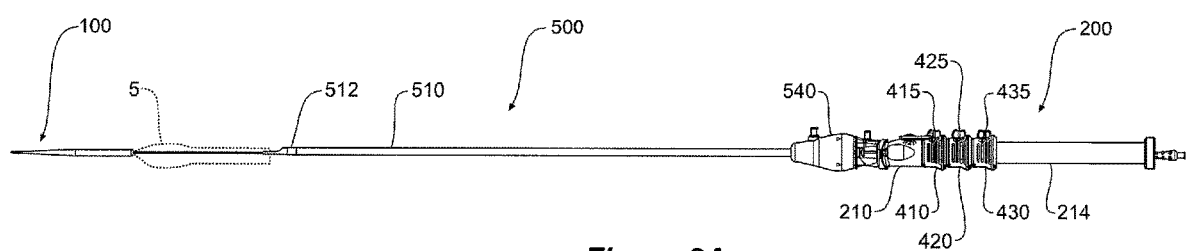
FIG. 2A is a similar side view to that of FIG. 1A showing a sheath assembly in a retracted position.
Figure 2B:
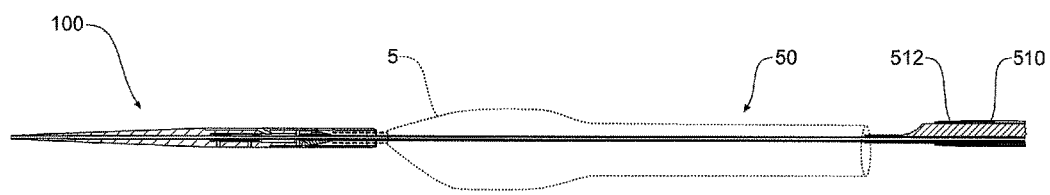
FIG. 2B shows a proximal end of the device of FIG. 2A.

The delivery device 10 also has an endograft receiving portion 50 for receiving the endograft 5 between the tip assembly 100 and the pusher catheter, as is shown in FIG. 2B. It should be understood that 'between' means that at least a portion of the endograft receiving portion 50 is between the tip assembly 100 and the pusher catheter.

The tip assembly slider 410 is operably connected to the inner handle portion 220 such that distal sliding movement of the tip assembly slider 410 slides the tip assembly 100 towards the pusher catheter 300. This is shown in the cross-sectional views of FIGS. 8A to 8D, 10, 12A, 12B, 13 and 14.

Figure 5:
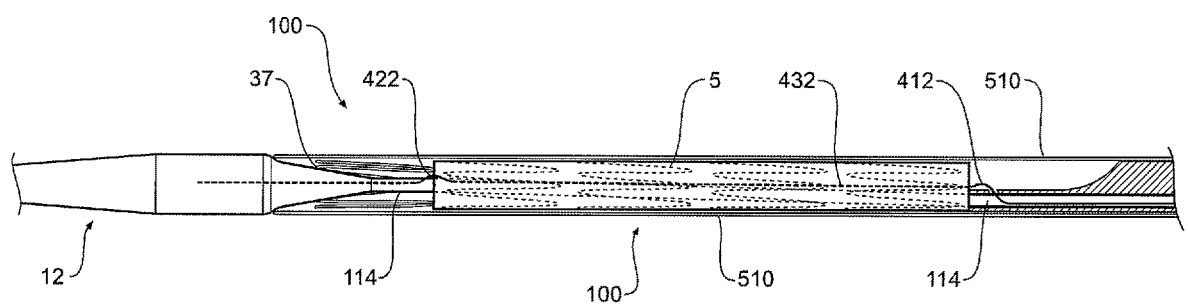
FIG. 5 is a detailed view of a proximal portion of the device shown in FIG. 1B.
Figure 12C:
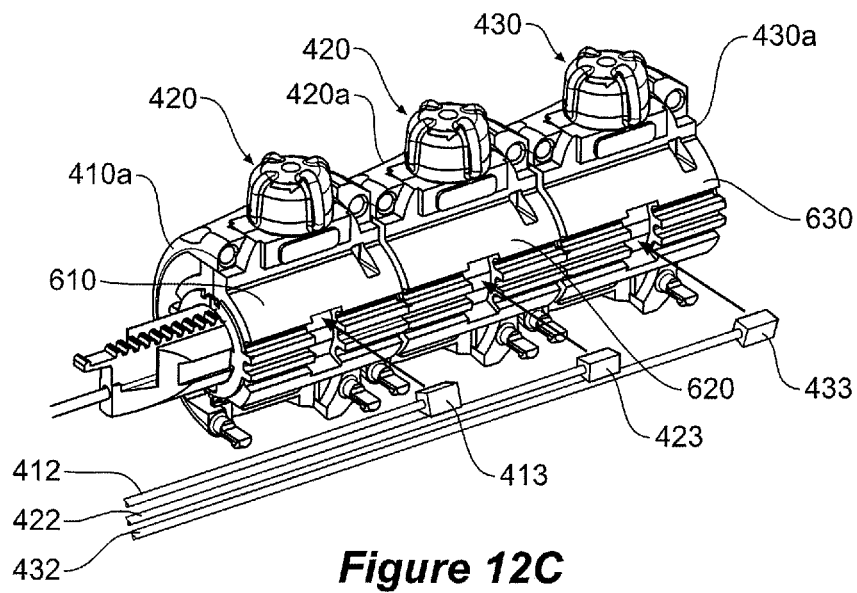
FIG. 12C shows a connection of trigger wires to a tip assembly slider, a proximal trigger wire release slider and a reducing trigger wire slider, all being components of the handle assembly shown in FIGS. 8A to 8D.
Figure 13:
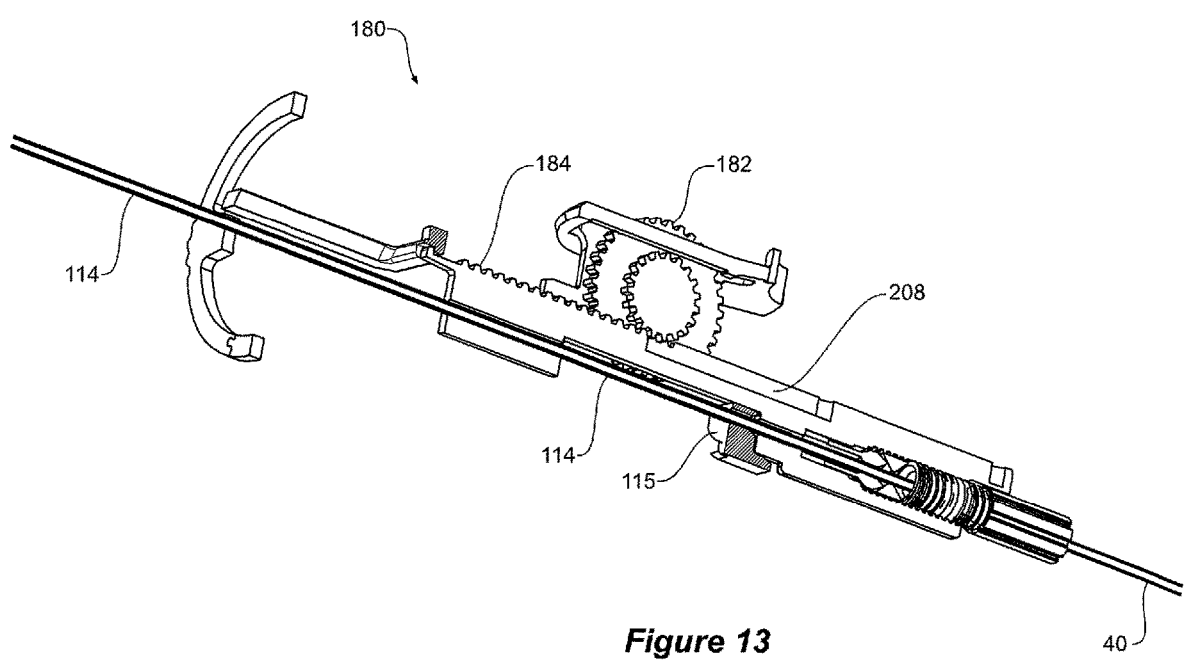
FIG. 13 is a similar view to that of FIG. 11, being a cross-sectional isometric view.

The delivery device 10 further comprises the distal trigger wire 412 referred to above for releasably retaining a distal end 9 of the endograft 5. A proximal end of the distal trigger wire 412 is shown in FIG. 5. FIG. 12C shows a distal end 413 of the distal trigger wire 412 locked to and terminating within the tip assembly slider inner 610, which forms part of the tip assembly slider 410 shown in FIGS. 12A and 12B. The routeing of the distal trigger wire 412 towards its distal end is shown in FIG. 10. FIG. 10 also shows the routeing of the proximal trigger wire 422 and the reducing trigger wire 432 wire towards their respective distal ends 423 and 433. Distal movement of the tip assembly slider 410 pulls the distal trigger wire 412 thereby releasing the distal end 9 of the endograft 5.

Figure 3A:
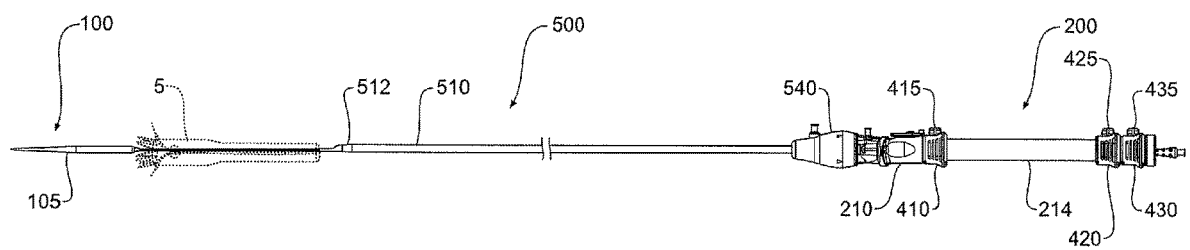
FIG. 3A is a similar side view to that of FIG. 2A showing an endograft in a partially released condition.
Figure 3B:
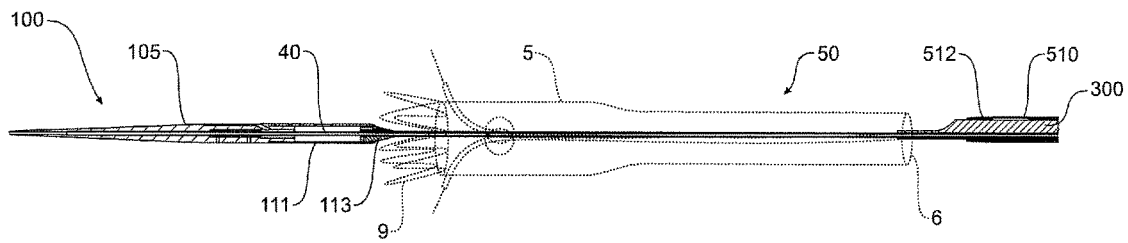
FIG. 3B shows a proximal end of the device of FIG. 3A.
Figure 4A:
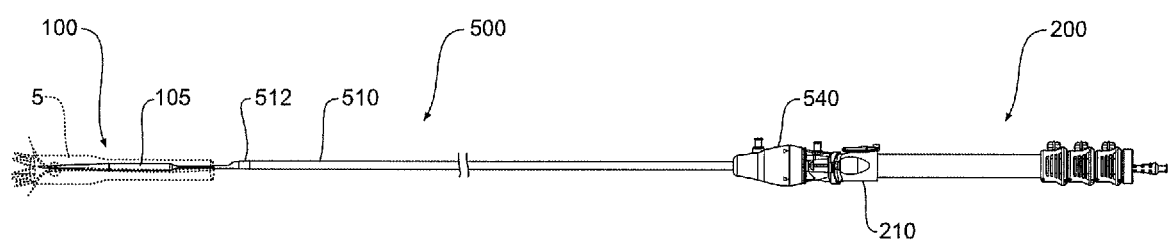
FIG. 4A is a similar side view to that of FIG. 3A showing the endograft in a fully released condition.
Figure 4B:
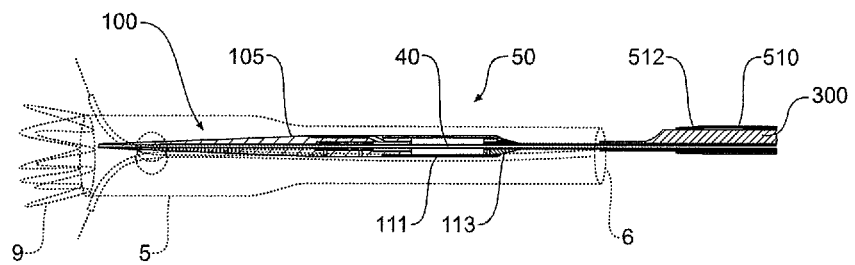
FIG. 4B shows a proximal end of the device of FIG. 4A.

Referring again to FIGS. 1A and 8A, it can be seen that the device 10 further comprises a proximal trigger wire release slider 420 mounted on the track 214 distally of the tip assembly slider 410, for sliding movement with respect to the track 214 from an initial position shown in FIGS. 1A, 2A and 8A to a triggered position shown in FIGS. 3A and 4A. The proximal trigger wire release slider 420 has an outer arcuate portion 420a and an inner arcuate portion 620, as is shown in FIG. 12C.

A proximal end of the proximal trigger wire 422 is shown in FIG. 5. The proximal trigger wire 422 is provided for releasably retaining the proximal end 6 of the endograft 5 which is loadable on the endograft receiving portion 50, again shown in FIGS. 2B and 5. Distal movement of the proximal trigger wire release slider 420 pulls the proximal trigger wire 422 thereby releasing the proximal end 6 of the endograft 5. This can be seen in the movement from the positions shown from FIGS. 6A to 6B.

FIG. 10 shows the proximal trigger wire 422 and its distal end 423 where it is locked to and terminates within the proximal trigger wire release slider 420, as shown in FIG. 12C.

Referring again to FIGS. 1A and 8A, it can be seen that the device 10 further comprises a reducing trigger wire release slider 430 mounted on the track 214 distally of both the tip assembly slider 410 and the proximal trigger wire release slider 420, for sliding movement with respect to the track 214 from an initial position shown in FIGS. 1A, 2A and 8A to a triggered position shown in FIGS. 3A and 4A. The proximal trigger wire release slider 430 has an outer arcuate portion 430a and an inner arcuate portion 630. The reducing trigger wire 432 is provided for holding the endograft 5 at a reduced diameter on the endograft receiving portion 50. Distal movement of the reducing trigger wire 432 pulls reducing trigger wire 432 thereby releasing the endograft 5 to expand radially. The precise arrangement for holding the endograft 5 at a reduced diameter on the endograft receiving portion 50 can vary. For instance, diameter reducing ties can be provided to achieve a reduction in the circumference of the stent graft 5 or other endograft 5, as is explained in the specification of U.S. patent application Ser. No. 11/507,115 titled "Assembly of Stent Grafts" which is hereby incorporated in its entirety into this specification. Other reduction arrangements may be used such as that disclosed by Australian Patent No 2012258395 "Assembly of Stent Grafts With Diameter Reducing Ties".

A proximal end of the reducing trigger wire 432 is shown in FIG. 5. FIG. 10 shows the reducing trigger wire 432 and its distal end 433 where it is locked to and terminates within the reducing trigger wire release slider 430, as shown in FIG. 12C.

As the drawings show, for instance FIGS. 1A, 2A and 8A, both the tip assembly slider 410 and the proximal trigger wire release slider 420 are mounted on the same track 214. Furthermore, in their initial positions, shown in 1A, 2A and 8A, they are hard up against each other. The effect of this is that the tip assembly slider 410 engages the proximal trigger wire release slider 420 such that it cannot be moved distally until after the proximal trigger wire release slider 420 has been moved distally, for instance, to the position shown in FIGS. 3A and 8B.

The tip assembly 100 includes a nose cone dilator 105, as indicated in FIG. 3A. In the embodiment shown in the drawings discussed above, and as is shown in FIGS. 6A and 6B, the tip assembly further comprises a top cap 111 and a retriever 113. An open configuration for the tip assembly 100 is shown in FIG. 6A and a closed configuration is shown in FIG. 6B. The top cap 111 comprises a distally facing mouth 112, whereby in the open configuration, the mouth 112 is open for receiving a proximal portion of the endograft 5 and in the closed configuration, the mouth 112 is closed by the retriever 113.

Figure 14:
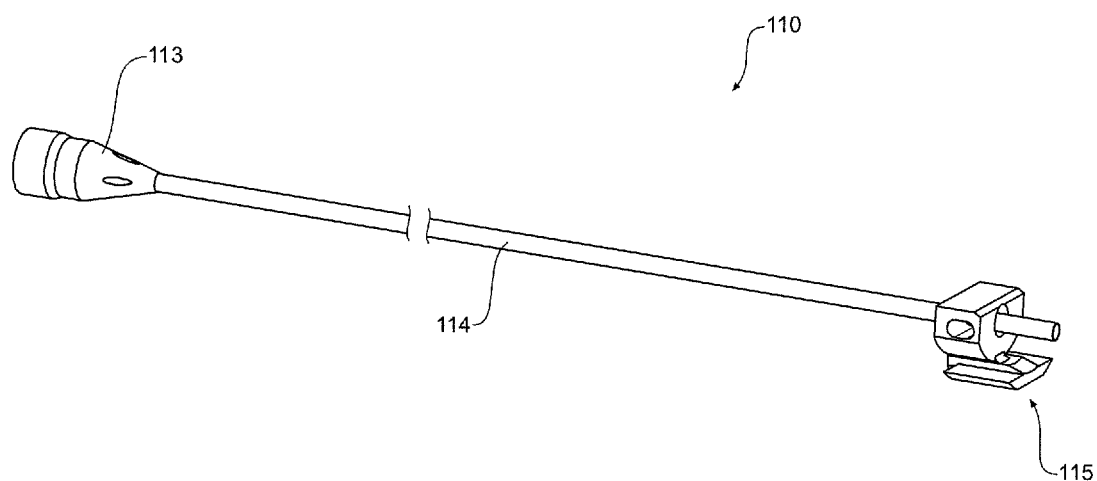
FIG. 14 is an isometric view of a tip retriever assembly which is a component of the device of FIG. 1A.

Referring now to FIG. 14, a connector 114 extending from the tip assembly 100 to the inner handle portion 220 is shown. The connector 114 connects the retriever 113 to the proximal trigger wire release slider 420. The connector 114 includes a distal portion 115 slidably engageable with the inner handle portion 220, as shown in FIG. 10. The distal portion 115 is locked to the trigger wire release slider 420, as is shown in FIGS. 12A and 12B. Tabs 115' and 115" are captive within a recess 418 within halves of the trigger wire release slider 420. Tabs 115' and 115" are shown in FIG. 12B, as is a recess 418 which receives tab 115'.

The connector 114 described above comprises a tube portion coaxially mounted over the guide wire catheter 40. The tube portion joins the tip retriever 113 to the distal portion 115. FIGS. 6A and 6B clearly show how the connector 114 connects to the tip retriever 113 and how the tip retriever 113 moves within the top cap 111.

With the first embodiment of the invention, the connector 114 is a tube, for instance a tube made from PEEK (Polyether ether ketone). In other embodiments, the connector 114 could be a metal tube, a wire or a plurality of wires for instance. Many possible constructions that are to transmit or convey a force may be suitable.

Turning now to FIGS. 11A and 11B, a connector receiver portion 204 of the inner handle portion 220 for receiving the connector distal end is shown. It can be seen that the receiver portion 204 has two extreme positions. The first position is shown in FIG. 8A and in FIG. 11A. The second position is shown in FIG. 8B and in FIG. 11B.

Figure 8B:
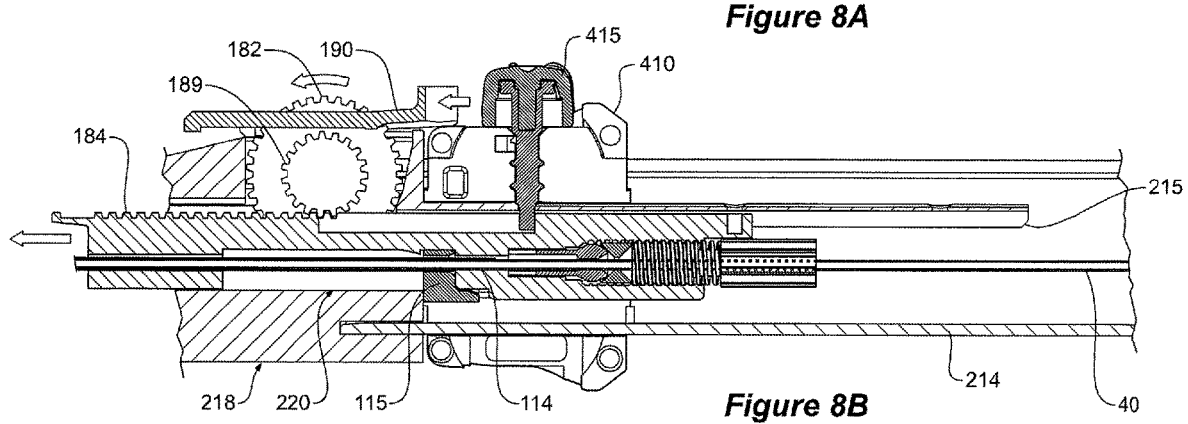
Figure 8C:
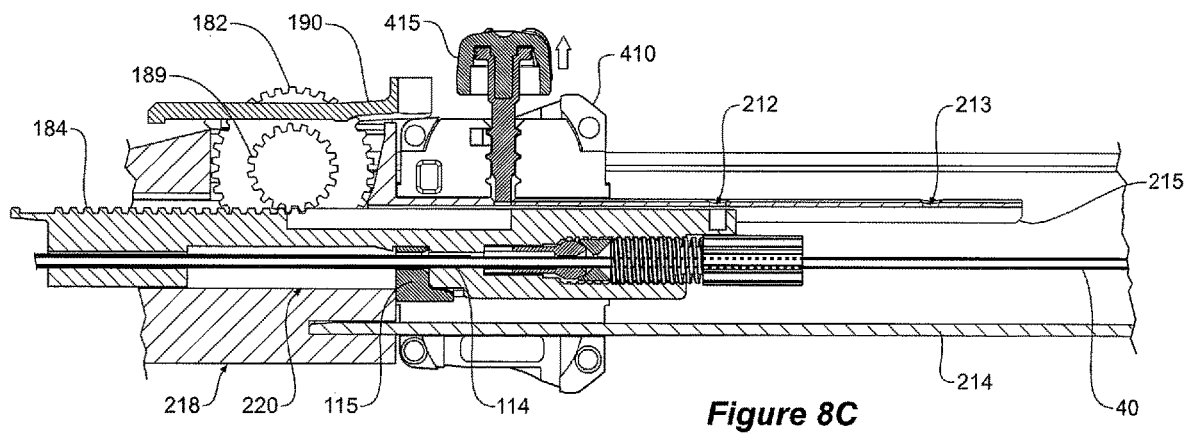

The connector receiver portion 204 locks to the connector distal portion 115 when the inner handle portion 220 moves to the proximal position shown in FIGS. 8B and 11B. While various locking arrangements may be used, with the first embodiment of the invention shown, the connector receiver portion 204 comprises a ramped portion 205 and a shoulder portion 206. The shoulder portion 206 abuts a surface 116, shown in FIG. 11A, of the connector distal portion 115 when the inner handle portion 220 is in the proximal position.

Referring to FIGS. 8A to 8D and to FIG. 10, it can be seen that the device 10 further comprises a tip assembly actuator 182 operably connected to the inner handle portion 220. An actuator receiving portion 184 on the inner handle portion is also provided. With the embodiment illustrated, the actuator receiving portion comprises a rack 184. The actuator receiving portion 184 (rack) is slidably drivable by the tip assembly actuator 182 in a proximal direction. The tip assembly actuator 182 is actuatable to move the inner handle portion 220 proximally with respect to the outer handle portion 210 thereby actuating the tip assembly 100 from the first configuration shown in FIG. 6A to the second configuration shown in FIG. 6B.

Referring to the sequence of FIGS. 8A to 8D, it can be seen that an interlock 190 is provided. This interlock 190 may be provided for some embodiments to prevent movement of the distal trigger wire release slider 410 to the triggered position until after the actuator 182 actuates the tip assembly 100 to the closed configuration shown in FIG. 6B.

Figure 8D:
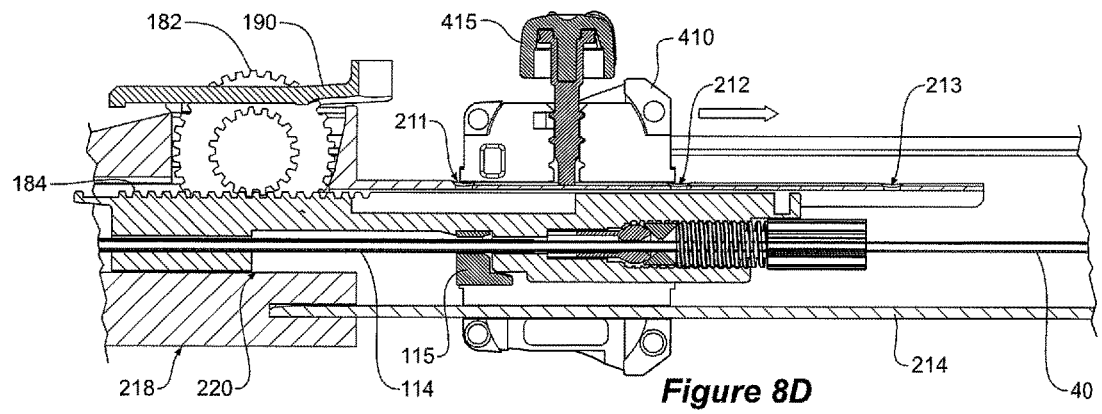
Figure 9:
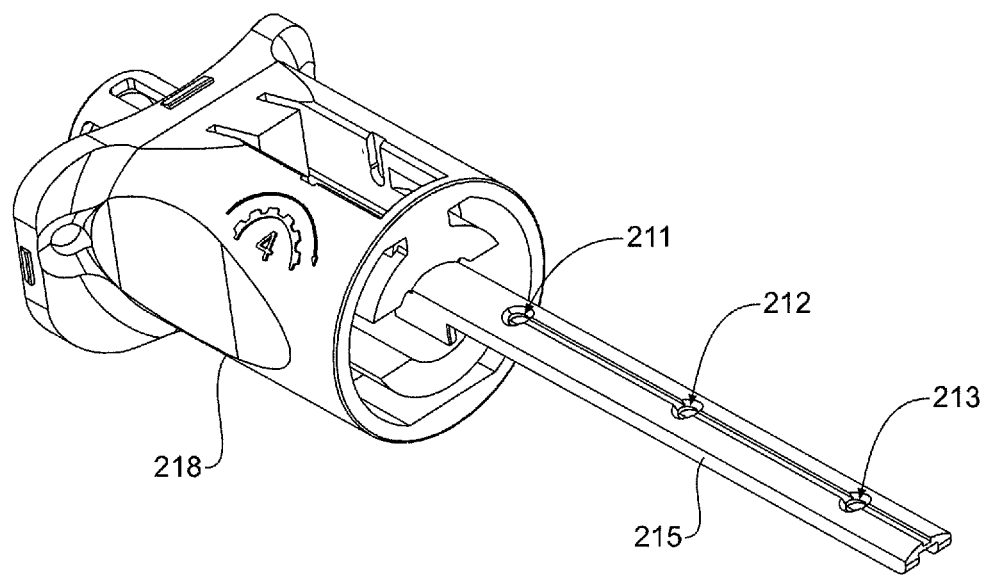
FIG. 9 is an isometric view of a component of the outer handle portion of the device shown in FIG. 1A.

Referring to FIG. 9, it can be seen that the outer handle portion 210 includes a handle tail 215. The handle tail 215 has recesses 211, 212 and 213 for receiving locks 415, 425 and 435 respectively. In the position shown in FIG. 8A, locks 415, 425 and 435 lock into respective recesses 211, 212 and 213. The interlock 190 referred to above and also shown in FIGS. 8A and 8B prevents rotation and unlocking of lock 415 when the device 10 is in the position shown in FIG. 8A. When the tip assembly actuator 182 is actuated to move the inner handle portion 220 proximally with respect to the outer handle portion 210, as is progressively shown moving from FIG. 8A to 8B, the interlock 190 is driven proximally away from the lock 415. This allows the lock 415 to be rotated and unlocked, as is shown in the movement from FIG. 8B to 8C. Its end is raised clear of the recess 211 (most clearly shown in FIGS. 9 and 8D) allowing the proximal trigger wire release slider 420, which is mounted on the track 214, to move distally as is shown in FIG. 8D.

Another embodiment of the invention will now be described with reference to FIGS. 15, 16A, 16B and 16C. This embodiment differs from the embodiment of FIGS. 1A to 14 primarily in relation to the tip assembly actuator and the locks located on the three sliders 410, 420 and 430.

Figure 15:
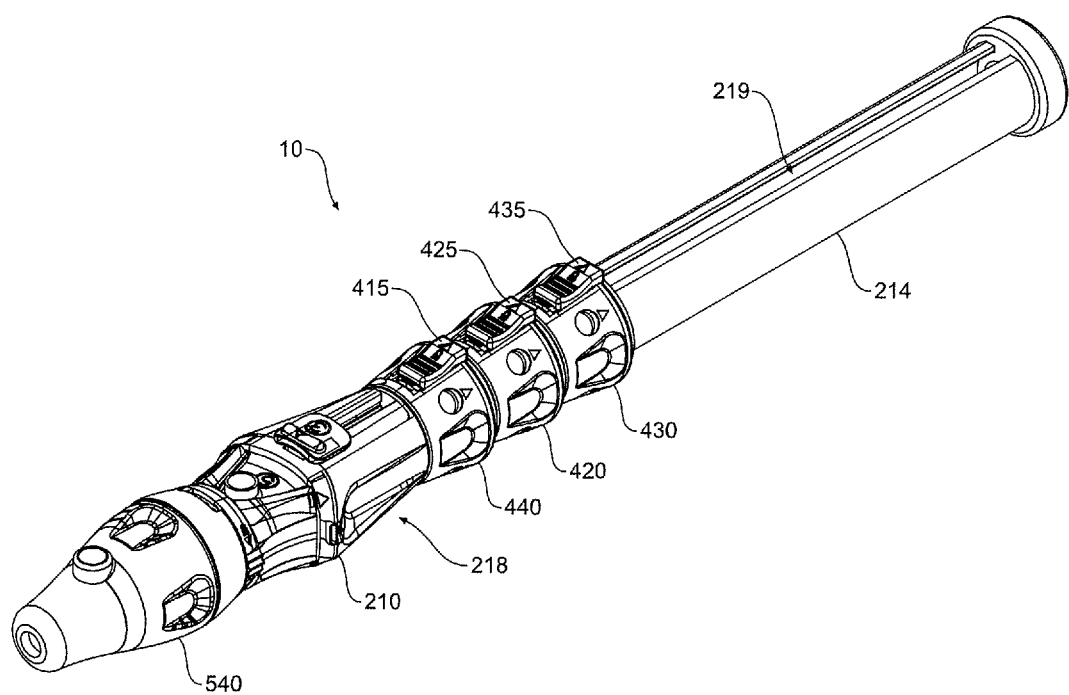
FIG. 15 is an isometric view of another embodiment of the invention.
Figure 16A:
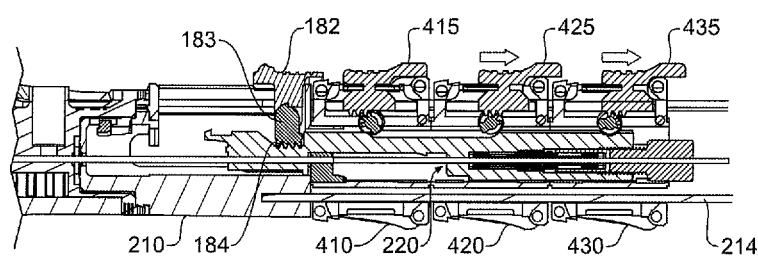
FIGS. 16A, 16B and 16C are cross-sectional views of the device shown in FIG. 15 in progressive positions.
Figure 16B:
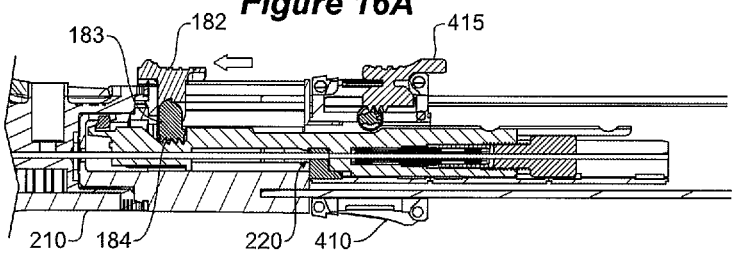
Figure 16C:
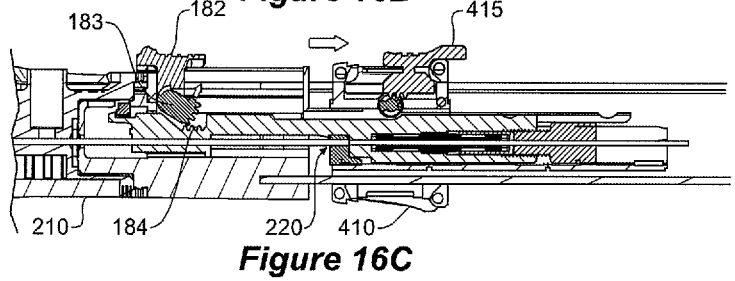

Referring to FIG. 15, as with the first-described embodiment, the delivery device 10 has an outer handle portion 210 mounted to its distal end 18. The outer handle portion 210 has a body portion 218 and a track 214 extending distally from body portion 218. The delivery device 10 of this embodiment also has an inner handle portion 220, which is shown in FIGS. 16A, 16B and 16C. Like with the first-described embodiment, the inner handle portion 220 is slidably movable within, and with respect to, the outer handle portion 210 from a distal position to a proximal position, as can be seen progressively in FIGS. 16A and 16B.

The tip assembly 100 of this embodiment is preferably identical to the tip assembly 100 of the first-described embodiment and is located at the proximal end 12 of the delivery device, as is shown in FIGS. 1A and 1B.

The delivery device 10 of this embodiment also has a pusher catheter 300, not shown in FIGS. 16A, 16B and 16C. The pusher catheter 300 is again identical to the pusher catheter 300 of the first embodiment of the invention as described above.

The delivery device 10 also has an endograft receiving portion 50 for receiving an endograft 5, which is identical to the endograft receiving portion 50 of the first-described embodiment, as is shown in FIG. 2B.

As with the first-described embodiment, the tip assembly slider 14 is operably connected to the inner handle portion 220 such that distal sliding movement of the tip assembly slider 14 slides the tip assembly 100 towards the pusher catheter 300. This is shown in the cross-sectional views of FIGS. 16A and 16B.

The trigger wires described with reference to the first-described embodiment are again the same with this embodiment.

The tip assembly slider 410 mounted on the rack 214 is generally similar to that of the tip assembly slider 410 of the first-described embodiment, with a different lock employed. While the lock 415 of the first-described embodiment was operable by a twisting motion, in contrast, the lock 415 of this embodiment is actuated by a pushing action.

A tip assembly actuator 182 for this embodiment can be seen in FIGS. 16A to 16D. This tip assembly actuator 182 is operably connected to the inner handle portion 220. The tip assembly actuator 182 is slidably movable with respect to the outer handle portion 210. This is in contrast to the tip assembly actuator 182 of the first-described embodiment which has a thumbwheel. The tip assembly actuator 182 also includes a pawl 183, as is illustrated in FIG. 16A. The pawl 183 engages the rack 184, as can be seen in FIG. 16C. The pawl 183 pivots away from the rack 184 when the distal trigger wire release slider 410 is slid in a distal direction away from the outer handle portion 210.

Figure 17:
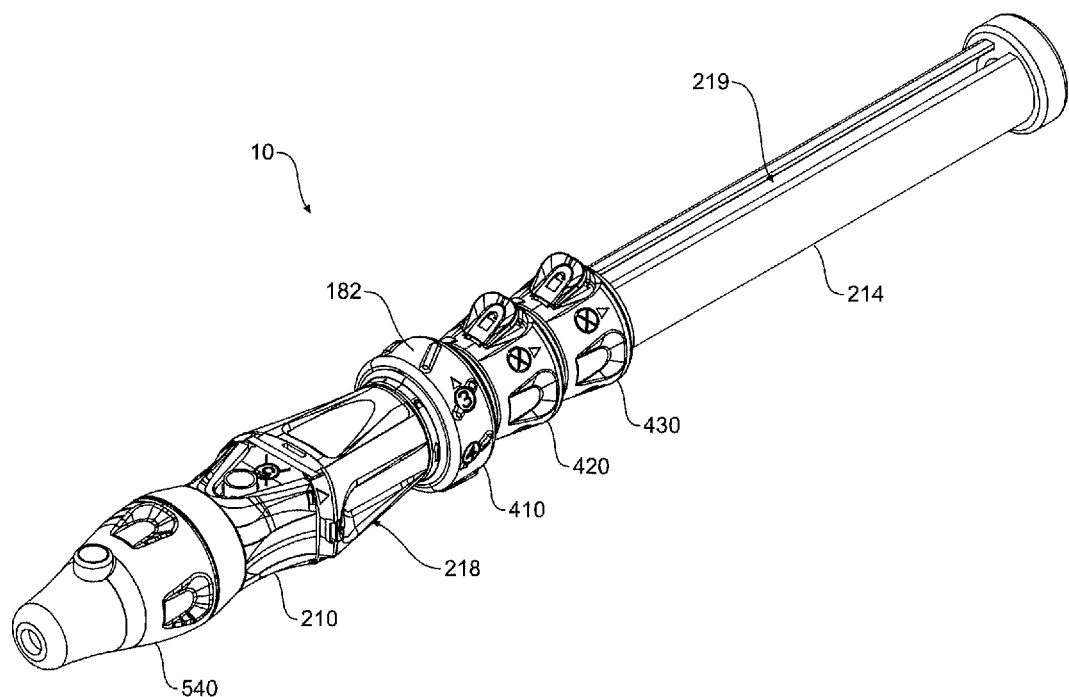
FIG. 17 is an isometric view of another embodiment of the invention.
Figure 18A:
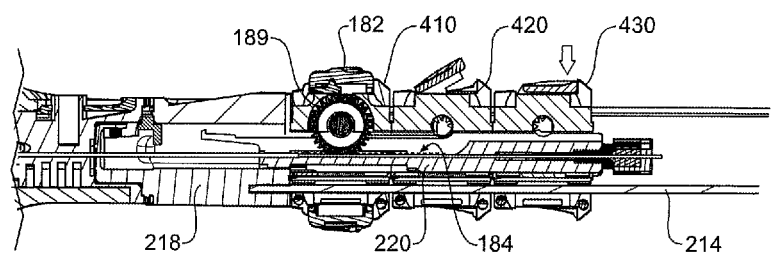
FIGS. 18A, 18B and 18C are cross-sectional views of the device shown in FIG. 17 in progressive positions.
Figure 18B:
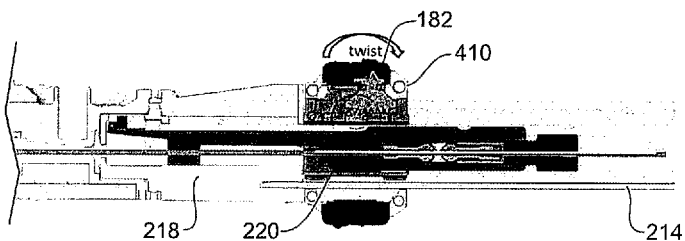
Figure 18C:
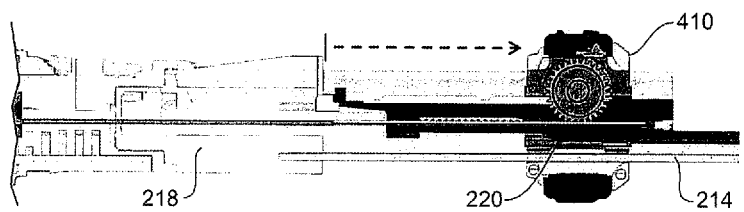

A further embodiment of the invention will now be described with reference to FIGS. 17, 18A, 18B and 18C. The tip assembly actuator 182 of this embodiment is actuated by twisting around a longitudinal axis of the device 10. Referring to FIG. 17, the tip assembly actuator 182 is marked with the numeral 3 and is operated by twisting. The twisting motion moves a pinion wheel 189 which engages a rack 184. Twisting of the tip assembly actuator 182 therefore results in the inner handle portion 220 being pushed forward in a similar way to that of the first-described embodiment.

Operation of the Device

Use or operation of the delivery device 10 will now be described. The operation will be described with reference to the first-described embodiment.

Referring first to FIG. 1A and its companion FIG. 1B, the delivery device 10 is shown together with a sheath assembly 500 in a configuration ready for use.

Typically, one of the first major steps in a procedure undertaken by a vascular surgeon would be to introduce a guide wire into a blood vessel, such as the femoral artery, using the Seldinger technique. This technique involves creating a surgical opening in the vessel of the needle and inserting a wire guide into the vessel through a bore of the needle. The needle is then withdrawn leaving the guide wire in place. The delivery device 10, as shown in FIGS. 1A and 1B, is then inserted over the guide wire and into the vessel.

Once the surgeon has positioned the proximal end 12 of the delivery device 10 near the target delivery area for the endograft 5, the sheath assembly 500 can be withdrawn to the position shown in FIGS. 2A and 2B. In this position, the sheath 510 of the sheath assembly 500 has been pulled back over the compressed endograft for stent graft 5 so as to expose it, as is shown in FIG. 2B. This step is conducted by "grounding" the outer handle portion 210 while pulling the valve body 540 of the sheath assembly 500 in a distal direction (away from the patient).

Typically, a next step in operating the delivery device 10 would be causing the stent graft to expand from its reduced condition to an expanded condition. This next step causes removal of the reducing trigger wire 432, the distal end of which can be seen most clearly in FIGS. 10 and 12C. In order to commence this step, the surgeon rotates the locking nob 435 from its position shown in FIG. 8A. This releases the lock 435 from the recess 213 illustrated in FIG. 9. This allows the reducing trigger wire release slider 430 mounted on the track 214 to be slid in a distal direction from the position shown in FIG. 1A to the position shown in FIG. 2A to 3A.

When the surgeon slides the slider 435 from the position shown in FIG. 2A to the position shown in FIG. 3A, the wire 432, as shown in FIG. 10, is pulled in a distal direction and its proximal end moves free from the endograft 5 allowing it to expand. It can also be seen that this step moves the reducing trigger wire release slider 430 from its position hard up against the adjacent proximal trigger wire release slider 420 (as shown in FIGS. 1A and 2A) to a position longitudinally spaced apart from adjacent proximal trigger wire release slider 420.

Typically, the next step in the procedure would be to release the proximal trigger wire 422. This is done by twisting the lock 425 shown in FIG. 8A so as to raise it out of engagement with corresponding recess 212 shown in FIG. 9. After this has been done, the slider 420 can be finger gripped and slid in a distal direction along the track 214. Importantly, this cannot be done out of sequence. That is, the slider 420 cannot be moved before the slider 430.

The above described movement of the slider 420 to the position shown in FIG. 3A causes the proximal trigger wire 422 to be detached from the tip assembly 100, as is shown progressively between FIGS. 6A and 6B.

The next step is actuation of the tip assembly actuator 182 shown in FIGS. 8A and 8B. The surgeon pushes on the thumbwheel 182 in the direction of the arrow shown adjacent the thumbwheel 182 in FIG. 8B. This results in the inner handle portion 220 advancing in a proximal direction from the position shown in FIG. 8A to the position shown in FIG. 8B. The effect of this is that the guide wire catheter 40 and hence the nose cone dilator 105 and the top cap 111 is also advanced in a proximal direction from the position shown in FIG. 6A to the position shown in FIG. 6B while the connector 114 stays in the same position (as can be seen from FIGS. 11A to 11B). This results in the exposed stents 7 of the endograft 5 being released to the position shown in FIG. 6B while at the same time the tip retriever 113 seats against the distal end of the top cap 111, as is shown in FIG. 6B.

With the first-described embodiment, the rotation of the thumb wheel causes an interlock 190 to move from the position shown in FIG. 8A to the position shown in FIG. 8B. In turn, this allows the lock 415 to be rotated from the position shown in FIG. 8B to the position shown in FIG. 8C. Once this has occurred, the lock is disengaged from the recess 212 shown in FIG. 9 allowing the slider 410 to be moved from the position shown in FIG. 8C to the position shown in FIG. 8D and beyond in the direction of the arrow shown on FIG. 8D. This movement causes the entire tip assembly 100 to move from the position shown in FIG. 3B to the position shown in FIG. 4B. That is, the tip assembly slider 410, being operably connected to the inner handle portion 210, slides distally so as to move the tip assembly 100 towards the pusher catheter 300.

After this step, typically the sheath assembly 500 would be advanced in a proximal direction towards the tip assembly 100 into a position against or over the tip retriever 113 so that the entire delivery device 10 can safely be withdrawn through and out from within the deployed stent graft 5.

Operation of other embodiments of the invention, including the second and third described embodiments is largely similar. The differences in operation with the second-described embodiment is that the actuator 182 is a slide mechanism rather than a thumb wheel and it is located on the outer handle portion 210 and is completely separate from the slider 410. Another difference with the second-described embodiment is that the locks 415, 425 and 435 are push button actuated rather than twist actuated. In other respects, operation is very similar as is illustrated in FIGS. 16A, 16B and 16C.

With the third-described embodiment, the operation is quite similar to that described with respect to the first-described embodiment, but the actuator 182 is a twist mechanism integrated by the numeral 3 on FIG. 17.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiments with regard to the particular elements and/or features described or depicted herein. It will be appreciated that the invention is not limited to the embodiment or embodiments disclosed, but is capable of numerous rearrangements, modifications and substitutions without departing from the scope of the invention as set forth in the following claims.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in U.S. patent application No. 62/594,911 and Australian patent application number 2017/904881, from which this application claims priority, and in the abstract accompanying this application are incorporated herein by reference.

The invention claimed is:

1. An endovascular delivery device, for delivering an endograft, the device having a proximal end and a distal end, and comprising:
    an outer handle portion mounted to the distal end of the delivery device and including a body portion and a track extending distally from the body portion;
    an inner handle portion slidably moveable within and with respect to the outer handle portion from a distal position to a proximal position;
    a tip assembly slider mounted on the track for sliding movement with respect to the track;
    a tip assembly at the proximal end of the delivery device;
    a pusher catheter extending proximally from the outer handle portion;
    a guide wire catheter extending through the inner handle portion and through the pusher catheter, the guide wire catheter being affixed at a distal end is thereof to the inner handle portion and at a proximal end thereof to the tip assembly;
    an endograft receiving portion for holding an endograft between the tip assembly and the pusher catheter;
    wherein the tip assembly slider is operably connected to the inner handle portion such that distal sliding movement of the tip assembly slider slides the tip assembly towards the pusher catheter;
    a proximal trigger wire release slider mounted on the track distally of the tip assembly slider for sliding movement with respect to the track from an initial position to a triggered position;
    a proximal trigger wire for releasably retaining a proximal end of the endograft loadable on the endograft receiving portion, whereby distal movement of the proximal trigger wire release slider pulls the proximal trigger wire thereby releasing the proximal end of the endograft; and
    wherein the tip assembly slider engages the proximal trigger wire release slider such that the tip assembly slider cannot be moved distally until after the proximal trigger wire release slider has been moved distally.

2. A device according to claim 1, comprising a distal trigger wire for releasably retaining a distal end of the endograft, whereby distal movement of the tip assembly slider pulls the distal trigger wire thereby releasing the distal end of the endograft.

3. A device according to claim 2, wherein the tip assembly comprises a top cap and a retriever, the tip assembly having an open configuration and a closed configuration.

4. A device according to claim 3, wherein the top cap comprises a distally facing mouth, whereby in the open configuration, the mouth is open for receiving a proximal portion of the endograft, and in the closed configuration, the mouth is closed by the retriever.

5. A device according to claim 4, comprising a connector extending from the tip assembly to the inner handle portion, the connector including a distal portion slidably engageable with the inner handle portion.

6. A device according to claim 5, wherein the inner handle portion comprises a connector receiver portion for receiving the connector distal portion.

7. A device according to claim 6, whereby the connector receiver portion locks to the connector distal portion when the inner handle portion moves to the proximal position.

8. A device according to claim 7, wherein the connector receiver portion comprises a ramped portion and a shoulder portion, the shoulder portion abutting a surface of the connector distal portion when the inner handle portion is in the proximal position.

9. A device according to claim 4, wherein a connector comprises a tube co-axially mounted over the guide wire catheter, the tube joining the tip retriever to the connector distal end.

10. A device according to claim 9, comprising a tip assembly actuator operably connected to the inner handle portion; and an actuator receiving portion on the inner handle portion, the actuator receiving portion slidably drivable by the tip assembly actuator in a proximal direction.

11. A device according to claim 10, wherein the actuator receiving portion comprises a rack.

12. A device according to claim 11, wherein the tip assembly actuator is actuatable to move the inner handle portion proximally with respect to, the outer handle portion, thereby actuating the tip assembly from a first configuration to a second configuration.

13. A device according to claim 2, comprising a proximal trigger wire release slider mounted on the track distally of the tip assembly slider, for sliding movement with respect to the track from an initial position to a triggered position; and a proximal trigger wire for releasably retaining a proximal end of the endograft loadable on the endograft receiving portion, whereby distal movement of the proximal trigger wire release slider pulls the proximal trigger wire thereby releasing the proximal end of the endograft.

14. An endovascular delivery device, for delivering an endograft, the device having a proximal end and a distal end, the delivery device comprising: an outer handle portion mounted to the distal end of the delivery device, the outer handle portion having a body portion and a track extending distally from the body portion; an inner handle portion, the inner handle portion slidably moveable within, and with respect to, the outer handle portion from a distal position to a proximal position; a tip assembly slider, mounted on the track for sliding movement with respect to the track; a tip assembly at the proximal end of the delivery device, the tip assembly comprising a top cap and a retriever, the tip assembly having an open configuration and a closed configuration, the top cap comprising a distally facing mouth, whereby in the open configuration, the mouth is open for receiving a proximal portion of the endograft, and in the closed configuration, the mouth is closed by the retriever; a connector extending from the tip assembly to the inner handle portion, the connector including a distal portion slidably engageable with the inner handle portion; a pusher catheter extending proximally from the outer handle portion; a guide wire catheter extending through the inner handle portion and through the pusher catheter, the guide wire catheter being affixed at a distal end thereof to the inner handle portion and being affixed at a proximal end thereof to the tip assembly; an endograft receiving portion for receiving the endograft between the tip assembly and the pusher catheter; a distal trigger wire for releasably retaining a distal end of the endograft, whereby distal movement of the tip assembly slider pulls the distal trigger wire thereby releasing the distal end of the endograft; and a proximal trigger wire release slider mounted on the track distally of the tip assembly slider, for sliding movement with respect to the track from an initial position to a triggered position, wherein the tip assembly slider engages the proximal trigger wire release slider such that the proximal trigger wire release slider cannot be moved distally until after the proximal trigger wire release slider has been moved distally; wherein the tip assembly slider is operably connected to the inner handle portion such that distal sliding movement of the tip assembly slider slides the tip assembly towards the pusher catheter.

* * * * *